United States Patent [19]

Rosowsky

[11] Patent Number: 4,956,461
[45] Date of Patent: Sep. 11, 1990

[54] DESAMINO-AMINOPTERIN AND -METHOTREXATE

[75] Inventor: Andre Rosowsky, Needham, Mass.

[73] Assignee: Dana Farber Cancer Institute, Inc., Boston, Mass.

[21] Appl. No.: 398,077

[22] Filed: Aug. 24, 1989

Related U.S. Application Data

[63] Continuation-in-part of Ser. No. 259,859, Oct. 19, 1988, abandoned.

[51] Int. Cl.$^5$ .......................................... C07D 475/06
[52] U.S. Cl. .................................................. 544/258
[58] Field of Search ........................ 544/258; 514/249

[56] References Cited

U.S. PATENT DOCUMENTS 2,512,572  6/1950  Smith, Jr. et al. .................. 544/258
4,767,761  8/1988  Rosowsky ........................... 544/258

OTHER PUBLICATIONS

Proc. Amer. Assoc. Cancer Res., vol. 30, Mar. 1989, p. 474.
Roth et al., "2-Alkylamino Derivatives of Pteroylglutamic Acid," J. Am. Chem. Soc., vol. 73, pp. 2864–2868, (1951).
S. Zakrzewski, "The Mechanism of Binding of Folate Analogues by Folate Reductase*," J. Biol. Chem., vol. 238, pp. 1485–1490, (1963).
J. Mead, "Rational Design of Folic Acid Antagonists," Handbook of Experimental Pharmacology, vol. XXXVIII/1 (Springer–Verlag, 1974), pp. 52–75.
Roth, B. et al., J. Am. Chem. Soc., vol. 72, p. 1914 (1950).
Declerco et al., Compt. Rend., vol. 243, p. 2172 (1956).
Matthews, D. A. et al., Science, vol. 197, p. 452 (1977).
Matthews et al., J. J. Biol. Chem., vol. 253, p. 6946 (1978).
Bolin, J. T. et al., J. Biol. Chem., vol. 25, p. 13650 (1982).
Villafranca, J. E. et al., Science, vol. 222, p. 782 (1983).
Howell, E. E. et al., Science, vol. 231, p. 1123 (1986).
Benkovic, S. J. et al., Science, vol. 239, p. 1105 (1988).
Subramanian, S. et al., Proc. Natl. Acad. Sci., U.S.A., vol. 75, p. 3201 (1978).
Jones, T. R. et al., AACR Proc., vol. 28, p. 276 (1987).
Newell, D. R. et al., AACR Proc., vol. 29, p. 286 (1988).
Hynes, J. B. et al., AACR Proc., vol. 29, p. 281 (1988).
Rosowsky et al., Jour. Med. Chem., vol. 32, pp. 517–520 (1989).

Primary Examiner—Donald G. Daus
Attorney, Agent, or Firm—Fish & Richardson

[57] ABSTRACT

A compound having the structure

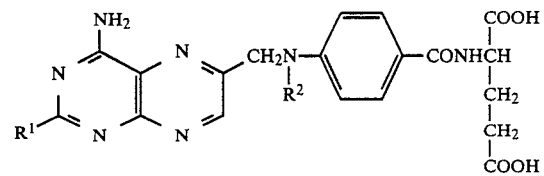

in which $R_1$ is hydrogen or a lower alkyl group and $R_2$ is hydrogen or methyl.

5 Claims, No Drawings

DESAMINO-AMINOPTERIN AND -METHOTREXATE

This invention was made with Government support and the Government has certain rights in the invention.

This application is a continuation-in-part of pending U.S. application Ser. No. 259,859 filed Oct. 19, 1988, now abandoned.

This invention relates to 2-desamino- and 2-desamino-2-lower alkyl-aminopterin and to 2-desamino- and 2-desamino-2-lower alkyl-methotrexate. By "lower alkyl" is meant an alkyl group having 1 to 5 carbon atoms, preferably methyl.

The 2-amino group in classical folic acid analogues such as methotrexate (MTX) and aminopterin (AMT) is conventionally thought to be an essential feature of the molecule where biological activity is concerned. Support for this view has come, historically, from the fact that analogues in which the 2-amino group was replaced by N,N-dimethylamino or methylthio groups were essentially devoid of activity, as reported in Roth et al., J. Am. Chem. Soc., Vol. 72, p. 1914 (1950) and De Clercq et al., Compt. rend., Vol. 243, p. 2172 (1956). More recently, much stronger support has been provided by X-ray crystallographic studies showing that the 2-amino group of MTX is involved in hydrogen bonding to a highly conserved aspartic or glutamic acid residue in the active site of the target enzyme dihydrofolate reductase (DHFR), as well as to a molecule of water which is hydrogen-bonded in turn to a threonine residue of the enzyme. Matthews et al., Science, Vol. 197, p. 452 (1977); Matthews et al. J. J. Biol. Chem., Vol. 253, p. 6946 (1978); Bolin et al., J. Biol. Chem., Vol. 25, p. 13650 (1982). Replacement of the aspartic acid residue in E. coli dihydrofolate reductase (DHFR) with serine by site-directed mutagenesis has been shown to produce a 3000-fold increase in the $K_D$ for MTX binding as measured by equilibrium dialysis. Villafranca et al., Science, Vol. 222, p. 782 (1983); Howell et al., Science, Vol. 231, p. 1123 (1986). This substantial change corresponds to a decrease of 4.4 kcal mol$^{-1}$ in the binding energy. In another study, Benkovic et al., Science, Vol. 239, p. 1105 (1988), replacement of the threonine residue by valine, whose side-chain cannot participate in hydrogen bonding, was found to produce a 25-fold decrease in the $K_D$ for MTX, a smaller effect nonetheless corresponding to a free energy difference of almost 2 kcal mol$^{-1}$. A further important role for the amino group is to provide resonance delocalization of the positive charge when $N^1$ is protonated during binding of MTX to DHFR, as reported in Subramanian et al., Proc. Natl. Acad. Sci., USA, Vol. 75, p. 3201 (1978). Thus, deletion of the 2-amino group has appeared to be a very unpromising approach to the design of DHFR inhibitors.

It has now been found that 2-desamino-aminopterin and 2-desamino-2 methyl aminopterin are in fact extremely weak inhibitors of the enzyme, dihydrofolate reductase (DHFR) with IC$_{50}$'s of 19 and >50 $\mu$M as compared with 0.02 $\mu$M for MTX. However, despite this >1000-fold loss of binding to DHFR, both compounds inhibited the growth of cultured human (WI-L2) and murine (L1210) tumor cells, with IC$_{50}$'s of 0.03–0.08 $\mu$M as compared with 0.01 $\mu$M for MTX. Moreover, both compounds were equivalent to AMT as substrates for folylpolyglutamate synthetase in vitro, showing that the 2-amino group is not essential for binding to this enzyme. Reversal studies using L1210 cells showed that neither 10 $\mu$M thymidine alone nor 100 $\mu$M hypoxanthine alone was fully protective. However, complete protection was observed in the presence of a combination of 10 $\mu$M thymidine and 100 $\mu$M hypoxanthine. The biochemical mechanism of action of these 2-desaminoaminopterin analogues and their polyglutamate metabolites is thus unlikely to involve any other site than the folate pathway. Rather, cell death is most probably due to inhibition of purine and pyrimidine biosynthesis by the parent compounds and/or their polyglutamates. The surprising capacity of 2-desaminoaminopterin and 2-desamino-2-methylaminopterin to inhibit tumor cell growth in culture shows that replacement of the 2-amino group in these classical 2,4-diamino antifolates by a hydrogen or methyl substituent markedly diminishes DHFR binding but does not abolish biological activity.

The compounds of the present invention are those having the structure

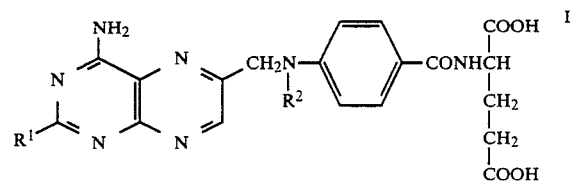

in which R$^1$ is hydrogen or lower alkyl, preferably methyl and R$^2$ is hydrogen or methyl. These compounds are a novel type of folate antagonist in which the 4-amino group of the classical antifolate structure is preserved but the 2-amino group is replaced by a nonpolar substitutent.

The following specific examples are intended to illustrate the nature of the invention and not to serve as a limitation upon its scope.

In the examples described below, IR spectra were recorded on a Perkin-Elmer Model 781 double-beam spectrophotometer (only peaks with wave numbers greater than 1250 cm$^-$ are listed). UV spectra were obtained on a Cary Model 210 instrument, and $^1$H NMR spectra on a Varian Model T60 instrument with Me$_4$Si or Me$_2$Si (CH$_2$)$_4$SO$_3$Na as the reference. TLC was performed on 250 $\mu$M silica gel plates (Analabs, North Haven, Conn.) or silica gel sheets (Eastman 13181) containing a fluorescent indicator. Spots were visualized under ordinary laboratory light or with 254 nm ultraviolet illumination in a viewing box. Unless otherwise specified, column chromatography was carried out on Baker 3405 silica gel (60–200 mesh) or Whatman DE-52 pre-swollen N,N-diethylaminoethylcellulose (DEAE-cellulose). HPLC was performed on a Waters C$_{18}$ radial compression cartridge (5 $\mu$M particle size, 0.5$\times$10 cm) connected to a Waters Model 400 instrument equipped with a Model 490 programmable multiwavelength detector and Model 660 programmable solvent gradient system. Melting points were taken in Pyrex capillary tubes in a Mel Temp apparatus (Cambridge Laboratory Devices, Inc.) and are not corrected. Starting materials were purchased from Aldrich, Milwaukee, Wisc., or synthesized according to the literature as indicated. DMF was dried over Davison 4A molecular sieves (Fisher, Boston, Mass.). Elemental analyses were performed by MultiChem Laboratories, Lowell, Mass., or Robertson Laboratory, Inc., Madison, N.J., and the values reported are within ±0.4% of theoretical values unless otherwise specified.

EXAMPLE 1

2-DESAMINO-AMINOPTERIN (a) Di-tert-butyl N-[4-[N-(2-amino-3-cyanopyrazin-5-yl) methylamino]-benzoyl]-L-glutamate 2-Amino-5-chloromethylpyrazine-3-carbonitrile (1.68 g, 0.01 mol) was added in small portions over 10 min to a stirred solution of di-tert-butyl N-(4-aminobenzoyl)-L-glutamate (3.78 g, 0.01 mol) and i-Pr$_2$NEt (1.74 mL, 1.29 g, 0.01 mol) in dry DMF (25 mL). After 20 hours at room temperature, the solvent was evaporated under reduced pressure and the residue was partitioned between CH$_2$Cl$_2$ and H$_2$O. The organic layer was evaporated and the product purified by column chromatography on a column of neutral Al$_2$O$_3$ (120 g, 3×24 cm) with 50:1 CHCl$_3$—MeOH as the eluent. Fractions containing the above-specified glutamate (R$_f$ 0.4, silica gel, 9:1 CHCl$_3$—MeOH) were allowed to evaporate passively in the hood until yellow crystals were formed; yield 3.60 g (59%); mp 71°–78° C; IR (KBr) 3400, 3210, 2990, 2940, 2230 (C≡N), 1730 (ester C=O), 1635, 1615, 1575, 1515, 1495sh, 1460, 1420, 1395, 1375, 1335, 1315, 1285, 1260 cm$^{-1}$; NMR (CDCl$_3$) δ 1.41 (s, γ-t-OBu), 1.48 (s, α-t-OBu), 2.0–2.4 (m, CH$_2$CH$_2$), 4.37 (m, 2H, CH$_2$NH), 5.35 (m, α-CH and NH), 6.61 (d, J=9 Hz, 3'- and 5'H), 7.67 (d, 9 Hz, 2'- and 4'-H), 8.22 (s, 6—H). Anal. (C$_{26}$H$_{34}$N$_6$O$_5$·0.8 CHCl$_3$) Calcd: C, 53.11; H, 5.79; N, 13.87. Found: C, 53.23; H, 5.94; N, 13.76.

(b) Di-tert-butyl N-[4-[N-(4-aminopteridin-6-yl)-methylamino]benzoyl]-L-glutamate A mixture of the product described in the preceding paragraph (a) (2.55 g, 0.005 mol), formamidine acetate (Aldrich, 2.08 g, 0.02 mol), and 2-ethoxyethanol (30 mL) was refluxed for 45 min, the solvent was evaporated under reduced pressure, and the dark residue was partitioned between CHCl$_3$ and H$_2$O. The emulsion was allowed to settle, and the residue after evaporation of the CHCl$_3$ layer was passed through a silica gel column (70 g, 3×35 cm), which was eluted first with 19:1 CHCl$_3$—MeOH to sequentially remove a brown impurity and yellow impurity, and then with 15:1 CHCl$_3$—MeOH to obtain the product. TLC homogeneous fractions (R$_f$ 0.5, Analab silica gel plates, 9:1 CHCl$_3$—MeOH) were combined, care being taken to exclude a colored impurity immediately following the product, and the solvent was evaporated to obtain 2-desaminoaminopterin as a tan powder (1.33 g, 58% yield); mp 103°–110° C., with sintering at lower temp; IR (KBr) 3370, 2980, 2940, 1730 (ester C=O), 1635, 1610, 1565, 1555, 1515, 1455, 1420, 1395, 1370, 1325, 1310, 1265 cm$^{-1}$; UV: λmax (95% EtOH) 248 nm (ε18,200), 289 (23,000), 338 (7,390); NMR (CDCl$_3$ δ1.40, (s, γ-t-OBu, 1.47 (s, α-t-OBu), 2.32 (m, CH$_2$CH$_2$, 4.70 (m, CH$_2$NH), 5.58 (m, α-CH), 6.60 (d, J=8 Hz, 3'- and 5'-H), 6.8–7.3 (m, 4—NH$_2$ and CONH), 7.67 (d, J=8 Hz, 2'- and 4'-H), 8.73 (s, 2—H), 9.05 (s, 7—H). Anal. (C$_{27}$H$_{35}$N$_7$O$_5$·0.25H$_2$O) Calcd: C, 59.82; H, 6.60; N, 18.09. Found: C, 59.74; H, 6.54; N, 17.90. Acidolysis of this di-tert-butyl ester product was carried out as follows to provide 2-desamino-aminopterin having the structural formula given above in which R$_1$ and R$_2$ are both hydrogen.

(c) A solution of the di-tert-butylester of paragraph (b) (1.23 g, 2.27 mmol) in 2:1 CH$_2$Cl$_2$—CF$_3$COOH (15 mL) was left to stand at room temperature for 2.5 hr and then poured into a separatory funnel containing 5% NH$_4$OH (100 mL) and CHCl$_3$ (50 mL). After some time to allow partitioning, the aqueous layer was reduced in volume under reduced pressure and the pH adjusted to 5 with 10% AcOH. The precipitate was collected and dried on a lyophilizer. Since the weight of the residue indicated probable entrapment of residual ammonium trifluoroacetate, the solid was redissolved in dilute NH$_4$OH and the acidification, filtration, and freeze-drying sequence was repeated to finally obtain 2-desamino-aminopterin as a dark yellow powder 2-desamino-aminopterin having the structure I shown above in which both R$_1$ and R$_2$ are hydrogen (1.0 g, ca. 40% yield); mp >300° C.; HPLC: 5% MeCN in 0.1M NH$_4$OAc, pH 7.0, flow rate 1.0 mL/min, retention time 12.2 min; IR (KBr) 3450, 2930, 1715, 1635, 1610, 1565, 1520, 1455, 1390, 1355, 1285, 1265 cm$^{-1}$; UV: λmax (pH 7.4) 246 nm (ε19,200), 285 (21,200), 333 (7,240); λmax (0.1 N NaOH) 246 nm (ε19,400), 285 (21,200), 333 (7,270); λmax (0.1N HCl) 293 (ε16,700); NMR (D$_2$O+K$_2$CO$_3$) δ 2.28 (m, CH$_2$CH$_2$), 4.47 (m, CH$_2$NH and α—CH), 6.55 (d, J=8 Hz, 3' and 5'H), 7.53 (d, J=8 Hz, 2'- and 4'-H), 8.33 (s, 2—H), 8.85 (s, 7—H). Anal. (C$_{19}$H$_{19}$N$_7$O$_5$—H$_2$O) Calcd: C, 1.48; H, 4.77; N, 22.11. Found: C, 51.48; H, 4.83; N, 21.95.

EXAMPLE 2

2-DESAMINO 2-METHYL-AMINOPTERIN (a) Di tert-butyl N-[4-[N-(4-amino 2-methylpteridin-6-yl)methylamino]-benzoyl]-L-glutamate A mixture of the product of paragraph (a) of Example 1 (2.55 g, 0.005 mol), acetamidine acetate (Aldrich, 2.95 g, 0.025 mol), and 2-ethoxyethanol (25 mL) was refluxed for 40 min, the solvent was evaporated, and the residue was partitioned between CHCl$_3$ and H$_2$O. The residue after evaporation of the organic layer was purified on a silica gel column (75 g, 3×35 cm), which was eluted with 19:1 CHCl$_3$—MeOH to obtain a crude product as a glass (1.8 g). Recrystallization from MeCN afforded the di tert-butyl ester pure as a yellow powder (two crops totaling 1.44 g, 60% yield); mp 105°-110° C.; IR (KBr) 3380, 2980, 2940, 1730 (ester C=O), 1630sh, 1610, 1570, 1550, 1515, 1455, 1420, 1395, 1370, 1355, 1335, 1305, 1280, 1260 cm$^{-1}$; UV λmax (95% EtOH) 249 nm (ε20,200), 290 (23,800), 341 (7,370); NMR (CDCl$_3$) δ1.42 (s, γ-t-OBu), 1.48 (s, α-t-OBu), 1.9–2.4 (m, CH$_2$CH$_2$), 2.68 (s, 2—Me), 4.72 (m, CH$_2$NH and α-CH), 5.28 (m, NH), 6.65 (d, J=9 Hz, 3'- and 5'-H, and overlapping s, 4—NH$_2$), 7.72 (d, J=9 Hz, 2'- and 4'-H), 9.23 (s, 7—H). Anal. (C$_{28}$H$_{37}$N$_7$O$_5$·H$_2$O) Calcd: C, 59.04; H, 6.90; N, 17.21. Found: C, 58.85; N, 6.55; N, 17.10. Acidolysis of this di tert butyl ester (1.27 g, 2.22 mol) was carried out using the same procedure as for the acidolysis step (c) of Example 1. The desired 2-desamino-2-methyl-aminopterin product having the structure I shown above in which R$_1$ is methyl and R$_2$ is hydrogen was obtained in a yield of 1.07 g (ca. 100%); mp >300° C.; HPLC: 10% EtOH in 0.1 M NH$_4$OAc, pH 7.5, flow rate 1.0 mL/min, retention time 10.2 min; IR (KBr) 3420, 3110, 2940, 2860, 1640, 1610, 1570, 1520, 1450, 1390, 1355, 1335, 1305, 1285, 1260 cm$^{-1}$; UV: λmax (pH 7.4) 247 (ε22,100), 285 (22,700), 337 (7,670): λmax (0.1 N HCl) 219 nm (ε20,900), 293 (19,700). Anal.

($C_{20}H_{21}N_7O_5 \cdot 1.5\ H_2O$) Calcd: C, 51.50; H, 5.19; N, 21.02. Found: C, 51.85; H, 4.93; N, 20.72.

Compounds having the structure I shown above in which $R_2$ is hydrogen and $R_1$ is ethyl or other lower alkyl group can be made by the same procedures using the appropriate amidine in place of formamidine or acetamidine in step (b) of Example 1 or step (a) of Example 2.

EXAMPLE 3

2-DESAMINO METHOTREXATE (a) 4-[N-(2-Amino-3-cyanopyrazin-5-yl)-N-methyl-]aminobenzoic Acid 2-Amino-5-chloromethylpyrazine-3-carbonitrile (3.38 g, 0.02 mol) was added in small portions over 5 min to a stirred solution of 4 (N-methylamino)benzoic acid (3.02 g, 0.02 mol) and i-Pr$_2$NEt (6.96 mL, 5.16 g, 0.04 mol) in dry dimethylformamide (40 mL). After 1.5 hours at room temperature, the solution was concentrated to ca. 15 mL under reduced pressure, and was added dropwise with stirring to H$_2$O (200 mL). After addition of 1 M HCl (2 mL, 0.02 mol), the mixture was stirred for 5 min, and the solid was collected and added to H$_2$O (100 mL) along with enough concentrated NH$_4$OH to make the solution strongly alkaline. Undissolved material was filtered off, the filtrate was acidified with 10% acetic acid, and the precipitate was collected and dried in vacuo at 90° C. over P$_2$O$_5$ to obtain 13 as a light yellow powder (3.72 g, 66%). The product was of sufficient purity to be used directly in the next step, but an analytical sample was obtained by applying portion of this material (0.2 g) on a DEAE cellulose column (1.5×25 cm, HCO$_3$-form), washing with a large volume of H$_2$O to remove salts, and eluting the product with 0.2M NH$_4$HCO$_3$. Fractions homogeneous by HPLC (10% MeCN in 0.1M NH$_4$OAc, pH 7.5, retention time 14.1 min) were pooled and freeze-dried, and the residue was taken up in dilute NH$_4$OH, reprecipitated with 10% AcOH, and dried as above; dec. >250° C.; IR (KBr) v 3400, 3200, 2930, 2840, 2670, 2570, 2245 (C≡N), 1680, 1615, 1570, 1535, 1495, 1435, 1390, 1335, 1305, 1280 cm$^{-1}$; NMR (d$_6$-DMSO) δ3.03 (s, Me), 4.51 (s, CH$_2$), 6.67 (d, J=9 Hz, 3'- and 5'-H), 7.15 (s, NH$_2$), 7.67 (d, J=9 Hz, 2' and 6'-H), 8.10 (s, 6—H). Anal. ($C_{14}H_{13}N_5O_2 \cdot 0.15H_2O$) Calcd: C, 58.80; H, 4.69; N, 24.49. Found: C, 59.03; H, 4.53; N, 24.06.

(b) 4[N-(4-Aminopteridin-6-yl)methyl-N-methyl-]aminobenzoic Acid

A mixture of the product described in (a) above (1.73 g, 6.05 mmol) and formamidine acetate (3.18 g, 30.6 mmol) in 2 ethoxyethanol (30 mL) was placed in an oil bath pre-heated to 135° C. The mixture became homogeneous after a few minutes, but gradually a precipitate appeared. After being heated for 1 hour, the mixture was concentrated to ca. 10 mL under reduced pressure and diluted with H$_2$O (50 mL). The solid was collected, taken up in dilute NH$_4$OH, reprecipitated with 10% AcOH, filtered, and dried on a lyophilizer to obtain 14 as a light-yellow powder (1.71 g, 89%); dec >250° C.; HPLC: 10% MeCN in 0.1 M NH$_{4\ OAc,\ pH}$ 7.5, retention time 10.2 min. IR (KBr) v 3460, 2940sh, 2670sh, 1675sh, 1640, 1615, 1595sh, 1570, 1535, 1495, 1430, 1405sh, 1395, 1370, 1335, 1305, 1270, 1250sh cm$^{-1}$; NMR (d$_6$-DMSO) δ 3.27 (s, Me), 4.95 (s, CH$_2$), 6.83 (d, J=9 Hz, 3'- and 5'-H), 7.75 (s, J=9 Hz, 2'- and 6'- H), 7.8–8.2 (broad m, NH$_2$), 8.52 (s, 2—H), 8.93 (s, 7—H). Anal. ($C_{15}H_{14}N_6O_2 \cdot 0.5H_2O$): Calcd: C, 56.42; H, 4.73; N, 26.32. Found: C, 56.34; H, 4.86; N, 25.98.

(c) Di-tert-butyl N-[4-[N-(4-Aminopteridin-6-yl)methyl-N-methyl]amino]-benzoyl]-L-glutamate The product described in (b) above (160 mg, 0.5 mmol) was added in portions over 3 min to a solution of diethyl phosphorocyanidate (98 mg, 0.6 mmol) and triethylamine (278 μL, 202 mg, 2 mmol) in dry dimethylformamide (10 mL). After 20 min at room temperature, di-tert-butyl L-glutamate hydrochloride (177 mg, 0.6 mmol) was added in a single portion and the reaction was monitored by TLC (silica gel, 19:1 CHCl$_3$—MeOH) to follow the disappearance of activated intermediate (R$_f$0.4) and formation of product (R$_f$0 5). When reaction was complete, the solution was evaporated under reduced pressure and the residue partitioned between CHCl$_3$ and dilute NH$_4$OH. The CHCl$_3$ layer was evaporated and the residue purified by chromatography on a silica gel column (15 g, 1.5×23 cm with 19:1 CHCl$_3$—MeOH as the eluent. Pooled pure fractions were concentrated and transferred to a vial with the aid of CHCl$_3$. The solvent was evaporated under a stream of air and the residue dried in vacuo at 60° C. to obtain the product named in the heading of this paragraph as a hardened orange foam (181 mg, 66%); mp 88°–93° C.; IR (KBr) v 3440, 3230sh, 2990, 2940, 1735, 1635, 1615, 1565sh, 1560, 1555sh, 1515, 1455, 1425, 1390, 1375, 1355sh, 1310, 1260 cm$^{-1}$; NMR (CDCl$_3$) d 1.42 (s, y-t-OBu), 1.48 (s, α-t-OBu), 1.8–2.4 (m, CH$_2$CH$_2$), 3.23 (s, N$^{10}$—Me), 4.60 (broad m, 1 H, α-CH), 4.87 (s, CH$_2$N), 6.73 (d, J=9 Hz, 3'- and 5'-H, overlapping a broad m, NH$_2$), 7.73 (d, J=9 Hz, 2'- and 6'—H), 8.75 (s, 2—H), 8.93 (s, 7—H). Anal. ($C_{28}H_{37}N_7O_5 \cdot 0.75H_2O$: Calcd: C, 59.51; H, 6.87; N, 17.35. Found: C, 59.50; H, 6.87; N, 17.29.

(d) N-[4-[N-(4-Aminopteridin-6-yl)methyl-N-methyl-]amino]benzoyl]-L-glutamic Acid ("2-DesaminoMTX")

A solution of the diester described in paragraph (c) (180 mg, 0.319 mmol) in 2:1 CH$_2$Cl$_2$—CF$_3$COOH (3 mL) was allowed to stand at room temperature for 3 hours. The dark-purple solution was then poured into a separatory funnel containing CHCl$_3$ (20 mL) and 5% NH$_4$OH (20 mL). After partitioning, the aqueous layer was concentrated to ca. 10 mL, and the solution was applied onto a Dowex 50W-X2 column (2×25 cm, H$^+$form) which was eluted first with a large volume of H$_2$O and then with 3% NH$_4$HCO$_3$. Collected fractions were freeze-dried to a solid which was purified further on a DEAE cellulose column (1.5×25 cm, HCO$_3$-form) with 0.2M NH$_4$HCO$_3$ as the eluent. HPLC-pure fractions were pooled and promptly freeze-dried to obtain the desired 2-desaminoMTX as a light-yellow solid (92 mg, 61%); dec >300° C.; HPLC: 10% MeCN in 0.1 M NH$_4$OAc, pH 7.0, retention time 5.7 min; IR (KBr) v 3450, 2990sh, 1710sh, 1645, 1620, 1570, 1525, 1465, 1395, 1370sh, 1315, 1270 cm$^{-1}$; NMR (d$_6$-DMSO) δ 1.8–2.4 (m, CH$_2$CH$_2$), 3.20 (s, N$^{10}$-Me), 4.90 (s, CH$_2$N, overlapping another s, H$_2$O), 6.78 (d, J=Hz, 3'- and 5'-H), 7.65 (d, J=9 Hz, 2'- and 6'-H), 7.8–8.2 (broad m, NH$_2$), 8.47 (s, 2—H), 8.88 (s, 7—H); UV: $\lambda_{max}$ (pH 7.4) 219 nm (ε19,700), 246 (19,400), 303 (24,000), 345 infl (6,900); $\lambda_{max}$(0.1 N HCl) 223 nm (ε21,200), 305 (23,600), 343 infl (9,000). Anal. ($C_{20}H_{21}N_7O_5.0.5NH_3.1.5H_2O$): Calcd: C, 50.58; H, 5.41; N, 22.12. Found: C, 50.53; H, 5.60; N, 21.71.

EXAMPLE 4

2-DESAMINO-2-METHYLMETHOTREXATE (a)

4-[N-(4-Amino-2-methylpteridin-6-yl)methyl-N-methyl]aminobenzoic Acid

Reaction of the product described in Example 3(a) (1.42 g, 5 mmol) with acetamidine acetate (2.95 g, 25 mmol) in 2-ethoxyethanol (25 mL) exactly as in the synthesis of Example 3(b) gave the product named in the heading of this paragraph as a light-yellow powder (1.46 g, 86%); dec >250° C.; IR (KBr) v 3450, 3220sh, 2950sh, 2650, 2520sh, 1920–1850 broad, 1670sh, 1635, 1610, 1585, 1570, 1530, 1485, 1450sh, 1420, 1390, 1360, 1340sh, 1325, 1300, 1285, 1255 cm$^{-1}$; NMR (d$_6$-DMSO) δ 2.45 (s, 2—Me), 3.23 (s, N$^{10}$—, overlapping another s, H$_2$O), 4.88 (s, CH$_2$), 6.78 (d, J=9 Hz, 3'- and 5'—H), 7.68 (d, J=9 Hz, 2'- and 6—H, overlapping a broad m, NH$_2$), 8.83 (s, 7—H). Anal. ($C_{16}H_{16}N_6O_2.H_2O$): Calcd: C, 56.13; H, 5.30; N, 24.55. Found: C, 56.36; H, 4.95; N, 24.44.

(b) Di-tert-butyl N [4-[N-(4-Amino 2-methylpteridin-6-yl)methyl N-methyl]amino]benzoyl]-L-glutamate The product described in the preceding paragraph (171 mg, 0.5 mmol) was treated with diethyl phosphorocyanidate (163 mg, 1 mmol) and Et$_3$N (278 μL, 202 mg, 2 mmol) as described in Example 3(c), and di-tert-butyl L-glutamate (296 mg, 0.5 mmol) was added after 1 hour. TLC (silica gel (19:1 CHCl$_3$—MeOH) was used to monitor for the formation of product (R$_f$0.6) and consumption of activated intermediate (R$_f$0.5). An extra 100-μL portion of Et$_3$N had to be added to drive the reaction to completion. After a work up identical to the one for the product of Example 3(c), the diester named in the heading of this paragraph was obtained as a hardened orange foam (200 mg, 69%); mp 91°–97° C.; IR (KBr) v 3440, 3240sh, 2990, 2940, 1735 (ester C=O), 1635, 1615, 1570, 1515, 1455, 1420, 1395, 1375, 1340, 1300, 1260 cm$^{-1}$; NMR (CDCl$_3$) δ 1.40 (s, y-t-OBu), 1.47 (s, α-t-OBu), 2.1–2.4 (m, CH$_2$CH$_2$), 2.67 (s, 2—Me), 3.22 (s, N$^{10}$—Me), 4.60 (broad m, α-CH), 4.85 (s, CH$_2$N), 6.73 (d, J=9 Hz, 3'- and 5'—H, overlapping a broad m, NH$_2$), 7.72 (d, J=9 Hz, 2'- and 6'—H), 8.88 (s, 7—H). Anal. $C_{29}H_{39}N_7O_5.0.75H_2O$): Calcd: C, 60.14; H, 7.05; N, 16.93. Found: C, 60.14; H, 6.75; N, 16.90.

(c) N-[4-[N-(4-Amino-2-methylpteridin-6-yl)methyl-N-methyl]amino]benzoyl]-L-glutamic Acid (6) ("2-Desamino-2-methylMTX")

The diester described in the preceding paragraph (195 mg, 0.345 mmol) was hydrolyzed exactly as in Example 3(d) to obtain the desired 2-desamino-2-methylMTX as a light yellow solid (109 mg, 65%); dec >300° C.; HPLC: 10% MeCN in 0.1M NH$_4$OAc, pH 7.0, retention time, 8.6 min; IR (KBr) v 3420, 3220sh, 2950sh, 2600br, 1910br, 1700br, 1635, 1610, 1570, 1560, 1520, 1455sh, 1420sh, 1395, 1345, 1305, 1255 cm$^{-1}$; NMR (d$_6$-DMSO) δ 1.8–2.4 (m, CH$_2$CH$_2$), 2.45 (s, 2—Me), 3.22 (s, N$^{10}$—Me), 4.90 (s, CH$_2$N), overlapping another s, H$_2$O), 6.80 (d, J=8 Hz, 3'- and 5'—H), 7.68 (d, J=8 Hz, 2'- and 6'—H), 7.7–8.1 (broad m, NH$_2$), 8.87 (s, 7—H); UV:λ$_{max}$ (pH 7.4) 218 nm (ε20,300), 247 (21,300), 303 (24,200), 345 infl (7,100); λ$_{max}$ (0.1 N HCl) 222 nm (ε21,300), 305 (23,400), 345 infl (8,900).

Critically important to the successful purification of the end products of Examples 3 and 4 on diethylaminoethylcellulose was that the fractions were freeze dried as soon as possible after collection. When the 3% NH$_4$HCO$_3$ eluates were left to stand overnight in the refrigerator prior to freeze-drying, extensive decomposition occurred. Similar base-labile properties were observed for the AMT analogues of Examples 1 and 2; when solutions of these compounds in 0.1 N NaOH were examined by HPLC, rapid appearance of new peaks indicating a chemical reaction, was observed. Solutions in pH 7.4 phosphate buffer, on the other hand, were stable at room temperature for at least 24 h, and only after some time (t$_\frac{1}{2}$≈3 days) began to show UV changes suggestive of pyrimidine ring cleavage. This slow ring opening at physiologic pH could prove to be a useful property, since it might minimize longterm accumulation of these compounds (or their presumably more toxic polyglutamates) in liver and kidney.

Small samples (1 mg) of the end products of Examples 1 and 2 were treated at room temperature in 1M NaOAc (10 mL) containing ZnCl$_2$ (10 mg) with freshly thawed carboxypeptidase G$_1$ enzyme solution (0.3 μL, 4500 U/mL). In less than 15 min, glutamate hydrolysis was nearly complete according to HPLC analysis (20% MeCN 0.1M NH$_4$OAc, pH 7.5), which showed the disappearance of >95% of the starting material (Example 1, 2.5 min; Example 2, 2.89 min) and the appearance of new peaks (3.0 and 3.3 min) assumed to be the 2-desamino and 2-desamino-2-methyl derivates of 4-amino-4-deoxypteroic acid, respectively. Under identical conditions, clinical grade methotrexate (mainly the L-form, 3.0 min) was cleaved to 4-amino-4-deoxy-N$^{10}$-methylpteroic acid (4.0 min), whereas D MTX (4.0 min, pre-formed from clinical grade MTX by carboxypeptidase G$_1$ treatment) was resistant to further treatment with the enzyme. Since the enzyme carboxypeptidase G$_1$ is well known to cleave L-MTX to 4-amino-4-deoxy-N$^{10}$-methylpteroic acid under conditions that leave D-MTX unaffected, these results show that my desamino analogues are essentially pure L-enantiomers.

The 2 desamino aminopterin of Example 1 and the 2-desamino 2-methyl aminopterin of Example 2 as well as the 2-desaminomethotrexate and the 2 desamino-2-methylmethotrexate of Examples 3 and 4 were tested for activity against purified dihydrofolate reductase (DHFR) from human leukemic lymphoblasts (Wl L2 cells, Delcamp et al., Biochemistry, Vol. 22, 633 (1983)). Aminopterin and methotrexate were also tested for the purpose of comparison, with the results shown in Table 1 below. The products of the examples also inhibited effectively the growth of cultured human (Wl L2) and murine (L1210) tumor cells. as shown in Table 1.

TABLE 1

| Compound | DHFR IC$_{50}$(μM) | Cells (IC$_{50}$,μM) L1210 | WI-L2 |
|---|---|---|---|
| AMT | 0.025 (1.0) | 0.002 (1.0) | 0.0071 (1.0) |
| 2-DesaminoAMT | 19 (760) | 0.082 (41) | 0.081 (10) |

TABLE 1-continued

| Compound | DHFR IC$_{50}$(μM) | Cells (IC$_{50}$,μM) L1210 | WI-L2 |
|---|---|---|---|
| 2-Desamino-2-methylAMT | >50 (>2000) | 0.042 (21) | 0.028 (3.9) |
| MTX | 0.024 (1.0) | 0.009 (1.0) | 0.013 (1.0) |
| 2-DesaminoMTX | 5.8 (240) | 0.36 (40) | 0.23 (9.6) |
| 2-Desamino-2-methylMTX | >20 (>800) | 0.22 (24) | 0.33 (14) |

DHFR was isolated from MTX-resistant WI-L2 cells and purified by affinity chromatography. Numbers in parentheses are normalized relative to MTX or AMT as appropriate.

Moreover, both products of Examples 1 and 2 were eguivalent to aminopterin as substrates for folylpolyglutamate synthetase (FPGS) in vitro, as shown by the results set forth in Table 2.

TABLE 2

Relative Activity of Aminopterin (AMT), 2 desamino AMT and, 2-desamino-2-methyl AMT as substrates for mouse liver folylpolyqlutamate synthetase (FPGS)

| cmpd[a] | K$_m$ (μM) | V$_{max}$, relative | V$_{max}$/K$_m$, relative[b] |
|---|---|---|---|
| Aminopterin (AMT) | 22.8 ± 6.4 | 1.0 | 1.0 |
| Product of Example 1 | 26.4 ± 1.4 | 0.87 ± 0.09 | 0.74 ± 0.09 |
| Product of Example 2 | 31.7 ± 5.6 | 0.77 ± 0.01 | 0.06 ± 0.08 |

[a]FPGS was partially purified from mouse liver and kinetics constants were derived as described in Moran et al., Mol. Pharmacol., Vol. 27, 156 (1985). For AMT and the product of Example 1, n = 3; for the product of Example 2, n = 2.
[b]Relative to AMT in the same experiment.

Reversal tests using L1210 murine cells showed that neither thymidine alone nor hypoxanthine alone was fully protective, but complete protection was obtained using the combination of both, as set forth in Table 3:

TABLE 3

Effect of thymidine and hypoxanthine on the growth of L1210 cells in the presence of 2-desaminoaminopterin of Example 1 and 2-desamino-2-methylaminopterin of Example 2

| cmpd | IC$_{50}$ (μM) standard medium | + dThd | +Hx | + dThd and Hx |
|---|---|---|---|---|
| Product of Example 1 | 0.082 | 0.16 | 0.26 | >100 |
| Product of Example 2 | 0.042 | 0.13 | 0.16 | >100 |

TABLE 3-continued

Effect of thymidine and hypoxanthine on the growth of L1210 cells in the presence of 2-desaminoaminopterin of Example 1 and 2-desamino-2-methylaminopterin of Example 2

| cmpd | IC$_{50}$ (μM) standard medium | + dThd | +Hx | + dThd and Hx |
|---|---|---|---|---|
| Example 2 | | | | |

Thymidine (dThd) and hypoxanthine (Hx) were added at concentrations of 10 μM and 100 μM, respectively.

Consequently, the products of Examples 1 and 2 act primarily as antifolates, not as inhibitors of some unrelated process. It is also clear that they are not direct inhibitors of either thymidylate or purine synthesis.

Other products within the scope of the claims can be shown to exhibit properties analogous to those of the products of Examples 1 to 4.

What is claimed is:

1. A compound having the structure

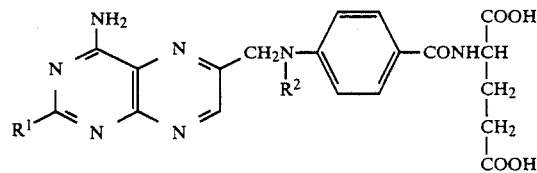

in which R$_1$ is hydrogen or a lower alkyl group and R$_2$ is hydrogen or methyl.

2. A compound as claimed in claim 1 in which R$_1$ is hydrogen and R$_2$ is hydrogen.

3. A compound as claimed in claim 1 in which R$_1$ is methyl and R$_2$ is hydrogen.

4. A compound as claimed in claim 1 in which R$_1$ is hydrogen and R$_2$ is methyl.

5. A compound as claimed in claim 1 in which R$_1$ is methyl and R$_2$ is methyl.

* * * * *

UNITED STATES PATENT AND TRADEMARK OFFICE
CERTIFICATE OF CORRECTION

PATENT NO. : 4,956,461
DATED : September 11, 1990
INVENTOR(S) : Andre Rosowsky

It is certified that error appears in the above-identified patent and that said Letters Patent is hereby corrected as shown below:

Column 4, line 24, "6 2.28" should be --$\delta$ 2.28--

Column 4, line 27, "C, 1.48;" should be --C, 51.48;--

Column 6, line 64, "(d, J=Hz," should be --(d, J=9 Hz,--

Column 8, line 43, "tc" should be --to--

Column 9, line 19, "eguivalent" should be --equivalent--

Column 9, line 25, "folylpolqlutamate" should be --folylpolyglutamate--

Signed and Sealed this

Twenty-fifth Day of February, 1992

Attest:

HARRY F. MANBECK, JR.

*Attesting Officer*                *Commissioner of Patents and Trademarks*